US007749192B2

(12) United States Patent
Hoffmann

(10) Patent No.: US 7,749,192 B2
(45) Date of Patent: Jul. 6, 2010

(54) ONE-WAY INJECTOR WITH CONTINUOUSLY CHARGED SPRING ENERGY STORE

(75) Inventor: Hans-Rainer Hoffmann, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 6 days.

(21) Appl. No.: 12/070,419

(22) Filed: Feb. 19, 2008

(65) Prior Publication Data
US 2008/0146997 A1    Jun. 19, 2008

Related U.S. Application Data

(63) Continuation-in-part of application No. PCT/EP2006/011747, filed on Dec. 7, 2006.

(30) Foreign Application Priority Data

Dec. 24, 2005  (DE) ................ 10 2005 062 206

(51) Int. Cl.
A61M 5/00    (2006.01)
A61M 5/30    (2006.01)
A61M 5/20    (2006.01)
(52) U.S. Cl. .................. 604/110; 604/68; 604/136
(58) Field of Classification Search .............. 604/110
See application file for complete search history.

(56) References Cited

U.S. PATENT DOCUMENTS

| | | | | |
|---|---|---|---|---|
| 3,797,488 A | * | 3/1974 | Hurschman et al. | ......... 604/136 |
| 4,874,367 A | * | 10/1989 | Edwards | ....................... 604/72 |
| 5,334,144 A | | 8/1994 | Alchas et al. | |
| 6,599,268 B1 | * | 7/2003 | Townsend et al. | ........... 604/110 |
| 2006/0258984 A1 | * | 11/2006 | Kiehne | ....................... 604/110 |

FOREIGN PATENT DOCUMENTS

| EP | 0 595 508 B1 | 5/1994 |
|---|---|---|
| FR | 1 174 719 A | 3/1959 |
| GB | 624 958 A | 6/1949 |
| WO | WO 95/31235 A | 11/1995 |

* cited by examiner

*Primary Examiner*—Nicholas D Lucchesi
*Assistant Examiner*—Jason Flick
(74) *Attorney, Agent, or Firm*—R. S. Lombard; K. Bach

(57) ABSTRACT

A one-way injector having a housing in which at least one mechanical spring energy store, at least one piston/cylinder unit, which can be at least temporarily filled with an active substance, at least one piston-actuating plunger and at least one tripping unit are arranged. To this end, the spring energy store comprises a preloaded spring element. The spring element is held in the preloaded position by a tension means surrounding at least a region of the spring. The tripping unit comprises a cutting tool which, in order to release the energy of the spring energy store, severs or weakens the tension means at least one point, the weakening immediately tearing the tension means. With the present invention, a one-way injector is developed which, with a small overall size, has only a few components and ensures reliable mounting and functioning with simple manipulation.

11 Claims, 3 Drawing Sheets

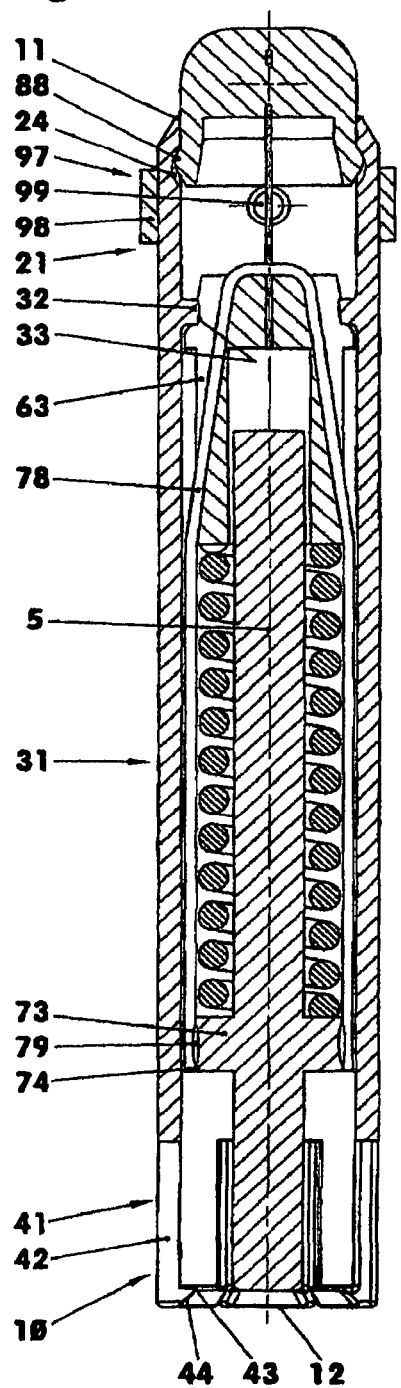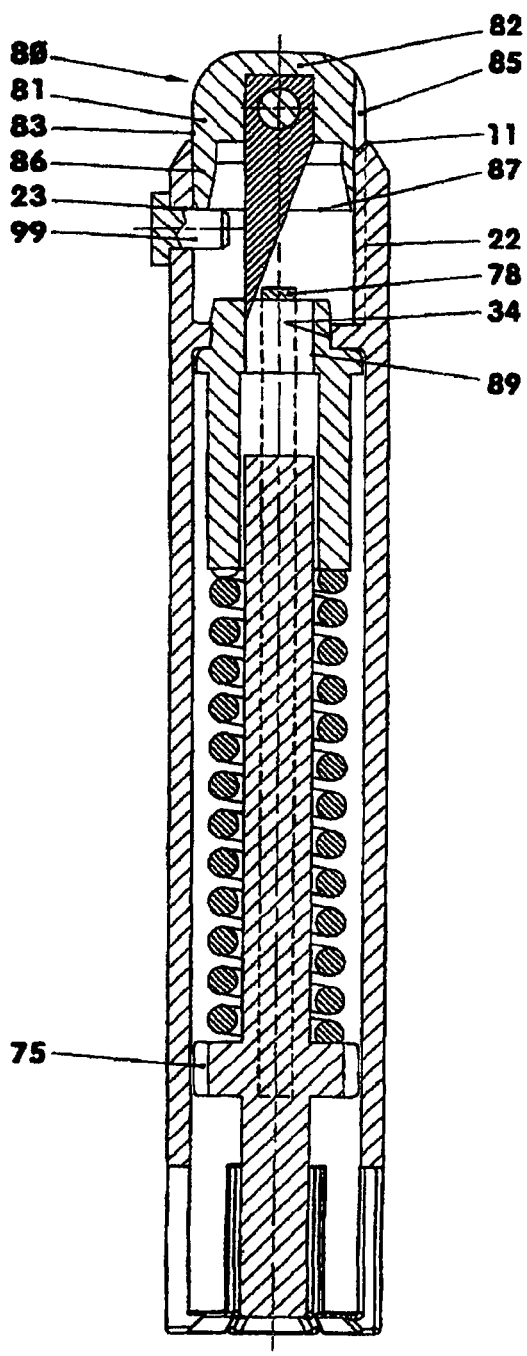

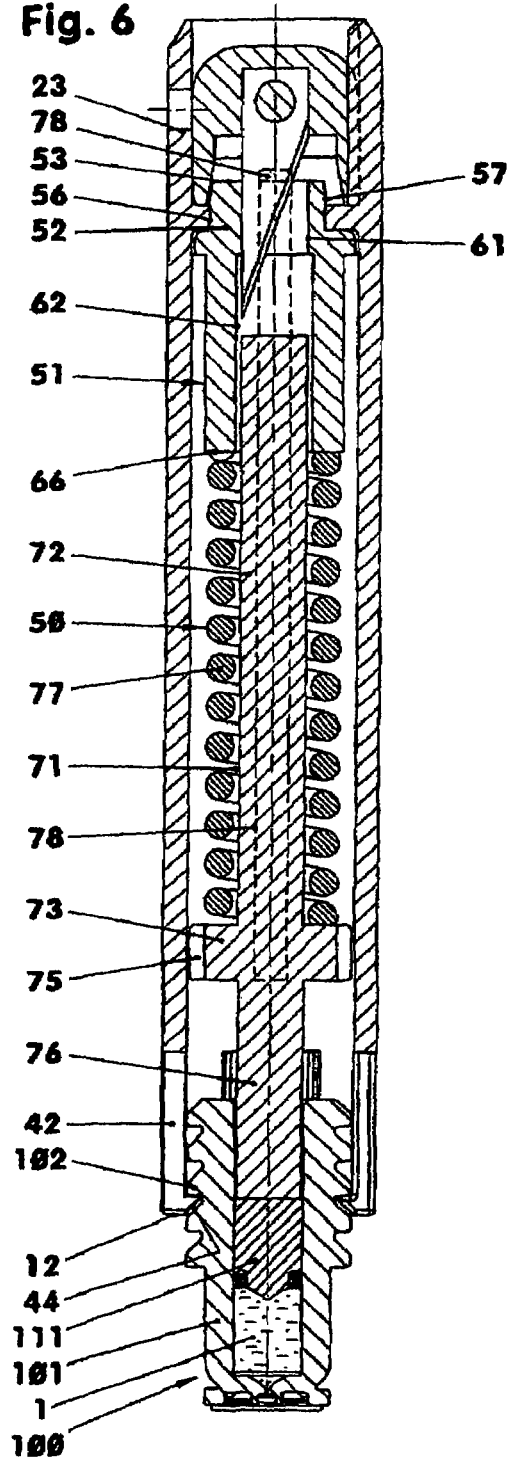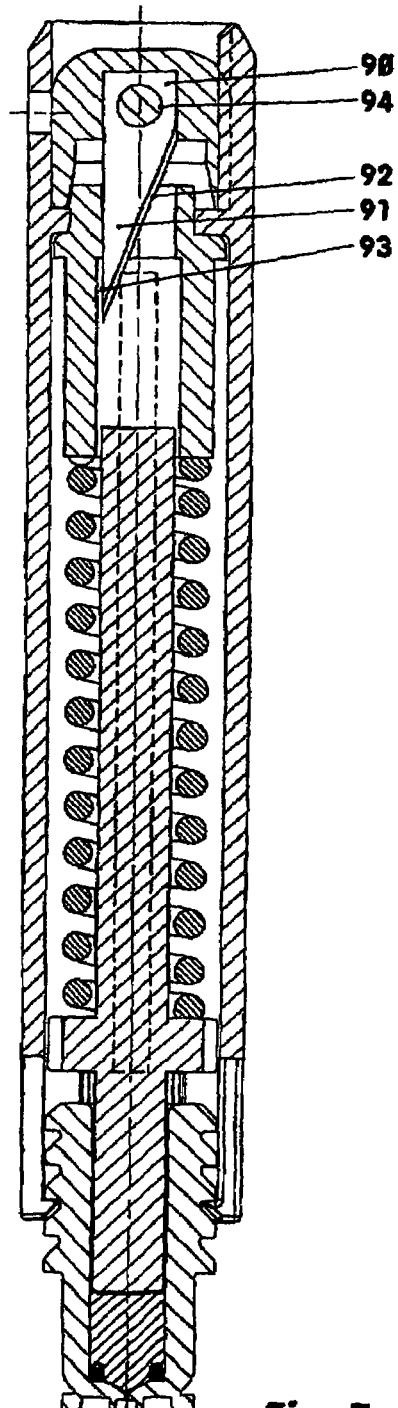

ONE-WAY INJECTOR WITH CONTINUOUSLY CHARGED SPRING ENERGY STORE

CROSS-REFERENCE TO RELATED APPLICATION

This is a continuation-in-part application of pending international application PCT/EP2006/011747 filed Dec. 7, 2006 and claiming priority of German Application No. 10 2005 062 206.2 filed Dec. 24, 2005.

BACKGROUND OF THE INVENTION

The invention relates to a disposable injector with a housing that contains at least one mechanical spring energy reservoir, at least one cylinder/piston unit that can be filled at least temporarily with active substance, at least one piston-actuating rod and at least one trigger unit.

An injector of this kind is known from EP 0 595 508 B1. It is constructed in such a way that the individual structural groups—namely the spring energy reservoir, cylinder/piston unit and trigger unit—cannot be separated from one another or handled separately. The trigger unit too is a complicated multi-part system.

A comparable device for injection of medicaments is also known from DE 695 06 521 T2, where the charged spring energy reservoir is secured by means of a breakable pin. When the breakable pin is broken by manual actuation, the spring that drives the syringe piston is released.

Moreover, DE 102 40 165 A1 describes a device for dosed ejection of a liquid active substance. In said device, the active substance is located in a syringe barrel. A syringe piston is spring-loaded and forced toward the active substance. The advance movement of the syringe piston is braked periodically by a band. The braking mechanism corresponds to the clock generator of a mechanical timepiece. The band is wound round the shaft of an escape wheel. The rotation of the escape wheel is triggered periodically at angles of rotation via an oscillating armature.

Therefore, the problem addressed by the present invention is that of developing a disposable injector of modular design which, with a small overall size, comprises only a small number of structural parts and, while being easy to handle, ensures reliable storage and reliable operation.

SUMMARY OF THE INVENTION

A one-way injector having a housing in which at least one mechanical spring energy store, at least one piston/cylinder unit, which can be at least temporarily filled with an active substance, at least one piston-actuating plunger and at least one tripping unit are arranged. To this end, the spring energy store comprises a preloaded spring element. The spring element is held in the preloaded position by a tension means surrounding at least a region of the spring. The tripping unit comprises a cutting tool which, in order to release the energy of the spring energy store, severs or weakens the tension means at, at least one point, the weakening immediately tearing the tension means. With the present invention, a one-way injector is developed which, with a small overall size, has only a few components and ensures reliable mounting and functioning with simple manipulation.

The spring energy reservoir for this purpose comprises a pretensioned spring element. The spring element is held in the pretensioned position by a pulling means that surrounds the spring in at least some areas. The trigger unit comprises a cutting tool which, in order to release the energy of the spring energy reservoir, severs the pulling means at least at one location, or weakens it, the weakening causing an immediate tearing of the pulling means.

With the present invention, a disposable injector is made available whose core feature is a spring energy reservoir with a pretensioned compression spring element, the spring energy being stored via a tensioned pulling means or a tensioning band or tensioning cable. The spring energy can be released only by irreversible mechanical destruction of the pulling means. A simple cutting tool is required for destruction of the pulling means. As regards the release of the spring energy, it is possible to dispense with a high-precision, multi-part mechanical locking system. The destruction of the pulling means also ensures that the injector cannot be reused in an inappropriate manner, for example as a dangerous toy catapult.

BRIEF DESCRIPTION OF THE DRAWINGS

Further details of the invention will become clear from the following description of an illustrative embodiment represented in the drawings, in which:

FIG. 1 shows schematically a disposable injector with charged spring energy reservoir, but without the cylinder/piston unit;

FIG. 2 shows a side view of FIG. 1 (six-way projection);

FIG. 6 shows a sectional view as in FIG. 2, but with the cylinder/piston unit, and with the trigger button pressed down;

FIG. 7 shows a sectional view as in FIG. 6, but with the spring energy reservoir discharged;

DETAILED DESCRIPTION OF THE PREFERRED EMBODIMENT

Figure 3:
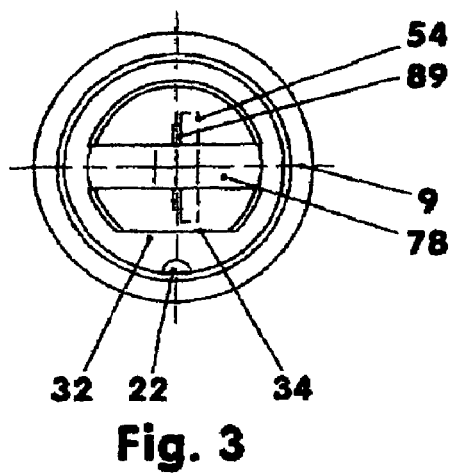
FIG. 3 shows a plan view of FIG. 1, but without the trigger button.

With references to FIGS. 1, 2 and 6 a disposable injector is shown with a permanently charged spring energy reservoir 50. The latter basically comprises a helical compression spring 77 that is pretensioned by means of a tensioning band 78. The spring energy reservoir 50 is accommodated in a housing 10, together with a trigger unit 80. The housing 10 also accommodates, if appropriate, a cylinder/piston unit 100, and the latter receives a medicament 1 that is to be administered.

The housing 10 is composed for the most part of a cylindrical tube, for example, which is divided into three functional areas 21, 31, and 41. According to FIGS. 1 and 2, the upper area is the trigger area 21. This is adjoined by the jacket area 31. An inwardly protruding middle flange 32 is arranged between both areas. The middle flange 32 has a central flange recess 33 which deviates geometrically from a circular cross section by a circle segment 34. The presence of the circle segment 34 is used to permit assembly in a manner secure against twisting, as will be described further below. The flange recess 33 is bevelled at least in some places from the direction of the jacket area 31.

Figure 4:
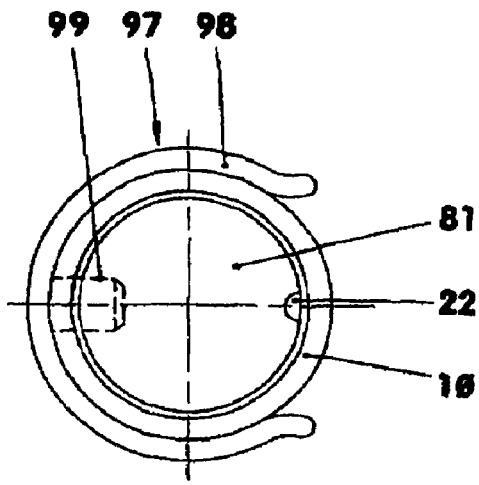
FIG. 4 shows a plan view of FIG. 2.

In the trigger area 21 of the housing 10, a transverse bore 23 is located between the top end face 11, in FIG. 2, and the middle flange 32. The transverse bore 23 serves to accommodate a trigger block 97. Opposite the bore 23, the inside wall of the housing 10 carries a lug 22 that provides protection against twisting. The lug 22 providing protection against twisting, and shown in plan view in FIGS. 3 and 4, is intended to allow a trigger button 81 of the trigger unit 80 to be fitted secure against twisting. The outer edge of the end face 11 is bevelled, for ergonomic reasons. Situated above the bore 23, and each offset by a 90 degree angle, there are two depressions 24, for example in the form of spherical cups, see FIG. 1, for locking the trigger button 81.

The fixing area 41 for receiving the insertable cylinder/piston unit 100 is situated, in the housing 10, below the jacket area 31, see also FIGS. 6 and 7. The fixing area 41 comprises, for example, six resilient hooks 42 that each end in an inwardly directed hook tip 43. In the direction towards the lower end face 12 of the housing, the hook tips 43 have a bevel 44 extending across the full thickness of the hooks. The length and the spring rate of the resilient hooks 42 are dimensioned such that the inserts 50, 100 required for the function of the disposable injector can be inserted without plastic deformation of the resilient hooks 42.

One of these inserts is the cylinder/piston unit 100, see FIG. 6. It is composed of a cylinder 101 and a piston 111. The cylinder 101 is, for example, a thick-walled pot whose optionally cylindrical outer wall has, for example, five peripheral locking ribs 102. The totality of the locking ribs 102 provides, in cross section, a saw-tooth profile, for example, the division between the tooth-like locking ribs 102 being equidistant. The maximum diameter of the locking ribs 102 is slightly smaller than the internal diameter of the housing 10 in the fixing area 41. The diameter of the areas lying between adjacent locking ribs 102 corresponds to the minimum diameter of the housing 10 in the area of the hook tips 43.

Figure 8:
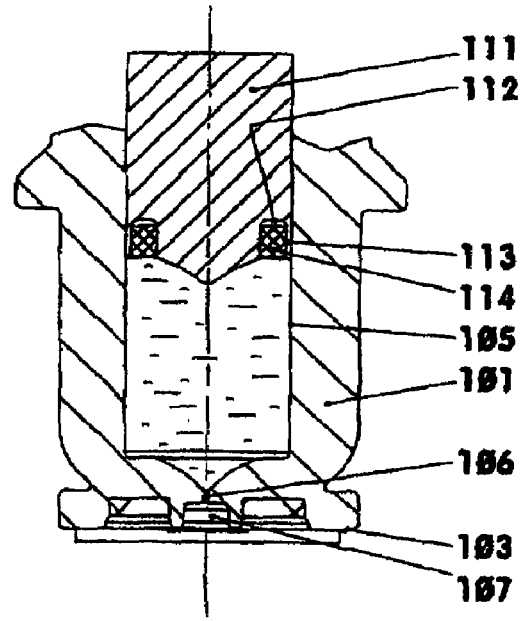
FIG. 8 shows a partial view of FIG. 6.

The rodless piston 111 sits in the, for example, cylindrical bore 105 of the cylinder 101, see FIG. 8. At its front end face, of at least approximately conical configuration, the piston 111 has an axial annular groove 112 for receiving a sealing ring 114 or a permanently elastic sealing compound. Lying between the outer wall of the annular groove 112 and, in the unloaded state, the cylindrical outer wall of the piston 111, there is an annular bar 113 whose wall measures, for example, only 0.2 millimeter. The bar 113 height is a multiple of the wall thickness of the bar.

A short cylindrical, nozzle-like bore 106 is located at the center of the bore 105 of the cylinder 101, whose cylinder base is adapted to the contour of the front end face of the piston. The diameter of the bore 106 is about 0.17 millimeter. This bore 106 is two to three times as long as its diameter. It opens out in a cylindrical recess 107 of the outer end face 103 at the bottom of the cylinder 101.

The spring energy reservoir 50 or the drive unit of the disposable injector is arranged between the piston 111 and the middle flange 32, see FIG. 6. The spring energy reservoir 50 comprises a helical compression spring 77, a piston-actuating rod 71, an anvil 51 and a tensioning band 78. The latter holds these parts together during the energy storage phase.

The piston-actuating rod 71 is divided into three areas which, for example, are substantially cylindrical. The lower area is the piston slide 76. Its diameter is slightly smaller than the internal diameter of the cylinder 105 of the cylinder/piston unit 100. The lower end face of the piston slide 76 acts directly on the piston 111.

The central area is the rod plate 73. The rod plate 73 is a flat and at least in some areas cylindrical disc whose external diameter is a few tenths of a millimeter smaller than the internal diameter of the housing 10 in the jacket area 31. The external diameter of the rod plate 73 is a few millimeters larger than the diameter of the opening formed by the tips 43 of the resilient hooks 42.

According to FIG. 1, the rod plate 73 has two rectangular grooves 74 lying opposite one another for receiving a pulling means 78, see FIG. 1. The rod plate 73 has, for example, two air admission grooves 75 arranged between the grooves 74.

The upper area adjoining the rod plate 73 is, for example, cylindrical spring-guiding bar 72. Its upper end projects with play into a central rod-guiding bore 62 of the anvil 51.

The anvil 51, see FIGS. 1, 2, 5 and 6, is a pot-shaped structural part whose base 52 has, for example, a rectangular, narrow recess 89 acting as knife-guiding slit 61. The radial outer contour of the base 52 has a locking groove 56 extending about part of the periphery. According to FIGS. 2, 3, 6 and 7, the base 52, in the area of the locking groove 56, has a lateral flattened area 57 that corresponds to the circle segment 34 of the middle flange 32.

Below the locking groove 56, the anvil 51 has a diameter that is only slightly smaller than the internal diameter of the housing 10 in this area. Two band-guiding grooves 63 extend between the anvil's lower end face 66, on which the helical compression spring 77 rests, and the upper end face 53. The respective bottom of these grooves 63 encloses with the center line 5 an angle of eight degrees, for example. The depth of the individual groove 63 increases in the direction of the upper end face 53 of the anvil 51.

The drive unit 50 can be preassembled as follows. The helical compression spring 77 is fitted onto the spring-guiding bar 72 so that it bears on the rod plate 73. The anvil 51 is placed onto the upper end of the piston-actuating rod 71. The helical compression spring 77 is compressed to the required length between the rod plate 73 and the anvil 51, for example in a special device not shown here. A tensioning band 78 is placed over the anvil 51 and the helical compression spring 77. The tensioning band 78 fitted in the band-guiding grooves 63 ends in the area of the plate grooves 74 of the rod plate 73. The two ends of the tensioning band 78 are fixed non-releasably in the plate grooves 74, for example by adhesion or welding 79. After the drive unit 50 has been removed from the special tensioning device, said drive unit 50 can be separately stored or is inserted directly thereafter into the housing 10 of a disposable injector.

Alternatively, the tensioning band 78 can also be secured on the rod plate 73 by a form-fit engagement. In this case it has, for example at each end, a widened area that sits in a respective corresponding recess of the rod plate 73.

The pulling means 78 in this illustrative embodiment has a rectangular solid cross section. It can also be elliptic, oval or circular. PVC-based plastics are proposed as suitable material, for example. The pulling means 78 can also be a cable or cord produced from yarns.

The trigger button 81, which carries a cutting tool 90, sits in a longitudinally displaceable manner in the trigger area 21 of the housing 10. The trigger button 81 has in principle the form of a bushing consisting of a base 82 and of a skirt 86. The cutting tool 90, for example with a single cutting edge, protrudes inwards from the base 82.

The trigger button 81 has a cylindrical outer wall 83 which, according to FIG. 2, has a semicircular groove 85 in the knife plane. The lug 22 belonging to the housing 10 and providing protection against twisting protrudes into the semicircular groove 85. In addition, the outer wall 83 has, in the lower area, two radially projecting cams 88 in mirror symmetry with respect to the knife plane. The cams 88 engage in depressions 24 of the trigger area 21 when the trigger button 81 is assembled and secured in place, see FIG. 1.

The knife blade 91 arranged in the base 82 of the trigger button 81 has, for example, the shape of a trapezium in side view, see FIGS. 2, 6 and 7. Three adjacent edges of the trapezium enclose two right angles; while the long edge 93 representing the reverse of the blade encloses an angle of, for example, 20° with the cutting edge 92. The blade reverse 93 is oriented parallel to the center line 5 of the device. It has a smooth surface. According to FIG. 1, the cutting edge 92 is ground symmetrically on both sides. In the assembled state according to FIG. 2, the flat reverse 93 of the blade is supported on and bears slidably on the corresponding wall of the knife recess 89. The width of the recess 89 is only slightly greater than the wall thickness of the knife blade 91, which is made of steel, for example.

The cutting tool 90 sits centrally and, for example, encapsulated, within the trigger button 81. For this purpose, it has a bore-shaped recess 94 to allow it to be secured with a force-fit or form-fit in the encapsulated area of the base 82.

Of course, the cutting tool can also have another shape and cutting geometry. For example, the cutting edge can be continuously curved, in such a way that the cutting angle increases as the stroke of the trigger button increases. It is also conceivable to equip the cutting tool with a double cutting edge, in which case the two cutting edges lie opposite one another. In this tool, the pulling means 78 is cut into simultaneously from two sides, that is to say transverse to the plane 9.

If, for example, a cable is used as the pulling means 78, the cutting tool can also be designed with two cutting edges directed away from each other. In this case, the knife blade cutting on both sides severs the cable centrally.

The skirt 86 has a lower and, for example, flat edge 87 which, upon actuation of the trigger button 81, serves as an abutment for the middle flange 32 of the housing 10. In the unactuated and secured state, the edge 87 bears on the blocking pin 99 of the trigger block 97.

The trigger block 97 is composed of the blocking pin 99 and of an open and resilient ring which supports the latter and which is in the form of an omega-shaped spring 98, see FIG. 4. The omega-shaped spring 98 sits on the outer wall of the housing 10 on the secured injector. It surrounds the outer wall by about 240 angle degrees. The blocking pin 99 engages in the bore 23. It protrudes a few millimeters into the inside of the housing 10, see FIG. 2. If appropriate, at least one of the free ends of the omega-shaped spring 98 is sealed with a paper or foil wrapper.

To assemble the disposable injector, the for example prefabricated drive unit 50 is fitted into the still empty housing 10. The drive unit 50 is locked non-releasably in the middle flange 32 and secure against twisting via the flange recess 33. In a second step, the cylinder/piston unit 100 is fitted in the fixing area 41. Independently of this, the trigger block 97 is applied and, if appropriate, sealed. Finally, the trigger button 81 equipped with the cutting tool 90 is inserted into the housing 10 in a manner secure against twisting. The inserted trigger button 81 bears with its lower edge on the blocking pin 99. In addition, it is fixed in the depressions 24 of the trigger area 21 via the cams 88.

The distance between the trigger button 81 and the anvil 51 is chosen such that the tip of the knife blade 91 protrudes safely into the knife slit 89, but without touching the pulling means 78, see FIG. 2.

The insertion of the cylinder/piston unit 100 can, if appropriate, also be carried out by the user.

In order to administer the medicament contained in the cylinder/piston unit 100, the trigger block 97 is first removed by pulling it sideways, after any seal present has been destroyed. The primed disposable injector is placed normally on the application site, and the trigger button 81 is pressed down by the force of the thumb. The tensioning band 78 is severed by the trigger button 81 being pressed down, see FIG. 6. In the process, the downwardly moved knife blade 91 plunges the tensioning band 78 into the knife slit 89. The tensioning band 78 lying on the anvil 51 cannot escape from the cutting movement, since it is guided with lateral support by the wall of the band-guiding grooves 63.

Figure 5:
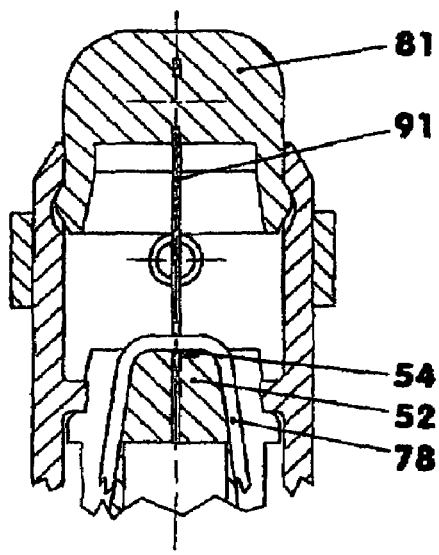
FIG. 5 shows a partial view of FIG. 1, with opposite cutting edge.

FIG. 5 shows the alternative combination of knife blade 91 and anvil 51. The knife blade 91 has an asymmetric cutting edge, i.e. the blade is ground only on one side. An opposite cutting edge 54, for example, of metal or ceramic, is additionally firmly embedded in the anvil 51, see also FIG. 3. The mutually facing cutting edges of the knife blade 91 and of the opposite cutting edge 54 form a shear in accordance with the principle of shearing. In this solution, the tensioning band 78 is sliced through with application of less force.

Depending on the material chosen for the tensioning band 78, it is not necessary to slice the tensioning band 78 through its entire cross section. It may suffice simply to nick the tensioning band 78 in order to cause it to immediately tear. In this case, the required stroke of the trigger button can be shortened.

Directly after the tensioning band 78 has been severed, the spring element 77 pushes the piston 111, via the forwardly moved piston-actuating rod 71, into the cylinder 101 in order to eject the product 1, see FIG. 7. The cylinder/piston unit 100 accommodates at least one component 1 of the product to be administered, such as, distilled water. The ejection process is completed when the piston 111 has reached the base of the cylinder 101.

A mechanical, force-enhancing gear may be arranged in the trigger unit 80, between the manually operated trigger button 81 and the cutting tool 90.

What is claimed is:

1. In combination with a disposable injector with a housing (10) that contains at least one mechanical spring energy reservoir (50), at least one cylinder/piston unit (100) for filling at least temporarily with active substance, at least one piston-actuating rod (71) and, at least one trigger unit (80), the improvement which comprises:

the at least one spring energy reservoir (50) comprising a pretensioned helical spring element (77) in mechanical communication with the at least one piston actuating rod (71), the at least one piston actuating rod (71) including a piston slide (76) proximate the lower area of the actuating rod (71) adapted to engage a piston (111) of the cylinder/piston unit (100), the piston (111) adapted to engage a cylinder (101) of cylinder/piston unit (100) upon actuation of the injector, a flat rod plate (73) proximate the central area of the actuating rod (71) adapted to support the helical spring (77), and a cylindrical spring-guiding bar (72) proximate the upper area of the actuating rod (71) adjoining the flat rod plate (73), the cylindrical spring-guiding bar (72) passing through the interior of the helical spring element (77), and a U-shaped tensioning band (78) adapted to surround the outer periphery of the spring element (77) in at least some areas on opposite sides thereof, an anvil (51) having a lower end face (66) and an upper end face (53), the lower end face (66) of the anvil (51) abutting the spring element (77), the anvil (51) disposed in operative position proximate the closed end of the U-shaped tensioning band (78), the anvil (51) having a pair of oppositely disposed band-guiding grooves (63) of predetermined depth therein extending between the lower end face (66)

and the upper end face (53) of the anvil (51), the spring element (77) is held in a pretensioned position by the tensioning band (78);

the trigger unit (80) comprising a manually actuated cutting tool (90), the cutting tool (90) in operative position proximate the closed end of U-shaped tensioning band (78) and adapted to cut the tensioning band (78) upon manual actuation thereof, the anvil (51) for providing a bearing for the tensioning band (78) to be severed by the cutting tool (90), the cutting tool (90) for triggering the release of energy of the helical spring element (77) by severing the tensioning band (78) at least in one location, or weakening it, the weakening causing an immediate tearing of the tensioning band (78) causing piston slide (76) to operatively engage piston (111) and piston (111) to operatively engage cylinder (101) to eject the active substance from cylinder (101).

2. The disposable injector according to claim 1, wherein the housing (10) is in one piece.

3. The disposable injector according to claim 1, wherein the tensioning band (78) is fixed non-releasably at both ends to the rod plate (73), and most of the cross-sectional centers of the tensioning band (78) lie parallel to the center line (5) of the element (77).

4. The disposable injector according to claim 1, further including a trigger button (8) adapted to carry the cutting tool (90).

5. The disposable injector according to claim 1, wherein the cutting tool (90) is a knife blade (91) with a single cutting edge (92).

6. The disposable injector according to claim 1, wherein the anvil (51) has a knife-guiding slit (61) therethrough for guiding the cutting tool (90).

7. The disposable injector according to claim 6, wherein anvil (51) includes opposite cutting edge (54).

8. The disposable injector according to claim 1, wherein the at least one energy reservoir (50) can be preassembled.

9. The disposable injector according to claim 1, wherein the at least one cylinder/piston unit (100) accommodates at least one component (1) of the substance that is to be administered.

10. The disposable injector according to claim 9, wherein the at least component (1) is distilled water.

11. The disposable injector according to claim 1, wherein the depth of each of the band-guiding grooves (63) of the anvil (51) increases in the direction of the upper end face (53) of the anvil (51).

* * * * *